Figure 1:
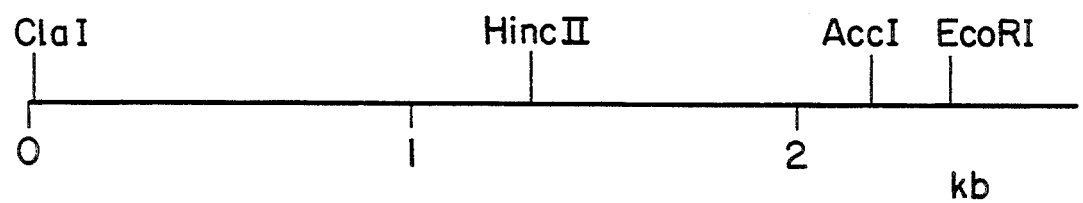

United States Patent [19]

Ueno et al.

[11] Patent Number: 5,441,881
[45] Date of Patent: Aug. 15, 1995

[54] NSP7524V RESTRICTION-MODIFICATION GENES

[75] Inventors: Takashi Ueno, Otsu; Hiroyuki Ito, Sapporo; Hirokazu Kotani, Moriyama; Kazuo Nakajima, Kyoto, all of Japan

[73] Assignee: Takara Shuzo Co., Ltd., Japan

[21] Appl. No.: 285,439

[22] Filed: Aug. 4, 1994

Related U.S. Application Data

[63] Continuation of Ser. No. 14,468, Feb. 5, 1993, abandoned.

[30] Foreign Application Priority Data

Feb. 21, 1992 [JP] Japan .................................. 4-069985

[51] Int. Cl.⁶ ........................ C12N 9/22; C12N 15/55; C12N 15/70
[52] U.S. Cl. .................. 435/199; 435/252.33; 435/320.1; 435/193; 536/23.2
[58] Field of Search ............... 435/193, 199, 252.33, 435/320.1; 536/23.2

[56] References Cited

U.S. PATENT DOCUMENTS 5,175,101 12/1992 Gotz et al. ........................ 435/172.3
5,202,248  4/1993 Vancott ................................ 435/199

OTHER PUBLICATIONS

Kupper, D., et al. (1989) Nuc. Acids Res 17(3), 1077–1088.
Card, C. O., et al. (1990) Nuc. Acids Res. 18(6), 1377–1383.
Piekarowicz, A., et al. (1991) Nuc. Acids Res. 19(8), 1831–1835.
Lunnen, K. D., et al. (1988) Gene 74,25–32.
Wilson, G. G. (1988) Gene 74,281–284.
"Nostoc PCC7524, a cyanobacterium which contains five sequence-specific deoxyriboncleases", Gene 20 (1982) pp. 103–110, John Reaston et al.

Primary Examiner—Charles L. Patterson, Jr.
Attorney, Agent, or Firm—Wenderoth, Lind & Ponack

[57] ABSTRACT

To provide Nsp7524V restriction-modification genes and a method for producing Nsp7524V restriction enzyme and Nsp7524V modification enzyme by using a novel microorganism having, introduced thereinto, plasmids containing said genes.

Nsp7524V restriction-modification genes. A method for producing Nsp7524V restriction enzyme and/or Nsp7524V modification enzyme which comprises incubating a microorganism carrying a plasmid having, integrated thereinto, Nsp7524V restriction-modification genes, and recovering the Nsp7524V restriction enzyme and/or Nsp7524V modification enzyme thus produced from the culture.

It becomes possible to efficiently produce Nsp7524V restriction enzyme and/or Nsp7524V modification enzyme which are useful in the field of genetic engineering.

8 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 2713 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
        ( A ) ORGANISM: Nostoc species
        ( B ) STRAIN: PCC7524
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

```
GATCCAGAAT ATGCACCCTT GGGTACGCAA ACTTATAGCC CAAAACCTTG TTCGCTAGAA      60

CGCCGGGCTT ATCTCTCAAG CAGTTCACCA ATGTATGTAG GTATGAATTT AGTTGGACGT     120

TGGTTATTGC CCATCTATCG CTTTGAGCCT ATCAAAAATC AAATCGATAC TTTACGAGGA     180

CATGGACGTA CCCATAAAGC CAAAGCAAAA TAGGTGATAG TTTCACAAGA AAAGTTAGG      240

AGGAGAGACA GCGCATTGTC GAGGTTTCCT CTGTTCCACT GTTATTTAAA TTTACTGATA     300

GTTGTAAATT GACTATATGC CATAATTACT AATTTTTTCA CCACCCTAAA TCCAGTCTAG     360

GGATTTGAGG CTTGTTTTCA ACAGTCGCGA TCGCACCCTT CGGTTCACTA ATCCCTATTA     420

TCGTGATTAC TTACCGTGGC TGCTGGGAGC GATACCTGCG GTAAGCTGCG CTAACGCACT     480

CATCGCCATA AAATTAAAGT ATGACTTTTG CTAAAACTTC TAAGTCTAAA CTATTTAAGA     540

TACTAGACTT TATCGGTCGC TTTTCGTCCC AAAAGACTAG AGATGAATAA AAATCTCTTG     600

CTAATGAAGA ATTTAAAAGC GCAACGGTTT TAAAGGCGAT TTCTTCATCC TCAAAACTGA     660
```

```
GAAAGTAAAC GTATCATCAA ATATAGTAGG TTTTTCAGAT ATTTTACCAA CCAATCTAAA      720
TTCTAATTTC TTGTAAAGTC CACAAATTGC AATTTTCCAA GGAGAAAAAC TATATGAGCC      780
AACACCAAAA ATAGAAAATC TTGGTTTGTT TTGATAGATT TTACTTTTTC TAGTATCTAA      840
TAATTTTTCA TGTTTTTCCA AATATTGCCA TGTTTAGGA  GCCAAATCTC TTATATTATC      900
AGTAGGTTCA CCAATAATTT TTTGAGTAAC CAAATATAT  CTGTCAGTCG CATTTATTTT      960
ATTCTGAGCA ACATAAGAAC CTTTGATTAA ACCCAAGAGA TAAGTTTCTT CTATATCAAC     1020
AATTTCTCCC AATCCATTTA TAAAAGTATC ATTAATTTTT TGTAATTCCA TTACACTCGC     1080
GCAATCATGC TTGATGCCGG AACGCCATTT TATATTTGAT TTATTAGTAT ATAAATTTTT     1140
TAACCTTTTT AAAGCAACCA AATCCTTGAT TAGAACATTG TTATGATAAC CTATACGATA     1200
GTATTTAGAA GTTTCAATAT TGTCAAATAT ATCACAAAAA TAGTTTTTG  ATATTAAATC     1260
AAATTTGCAT AAAAACAAAC AAGCGTCAAC ATTTACCCTA AAATACTTTC TTGTATCTAT     1320
TTTATAAGTT GCAGAGTAAG CTAGATTTAA TTTCTGAGAA TGAATATAGT TTAATATTTT     1380
CCTAGAAACA GAAGTTTTAC AAAGCATTGC TAGATAACCA TTATGCTTTT GCAAGCATTG     1440
CACAAGCCGA ATTAACATCC ATTCTGATAT ATCAAATTA  CTCTTACCAG TGATTGCATC     1500
TAATCCATGA TAGTTTTGAA AATTGTTCTT GATTGGCAAG TTTTCACCAT CAATACTACC     1560
TTGTTGTGAA TTTGTTACCC AAGGTAAATT ACCAATTATT AAAATTTCCT TATTTAATTG     1620
CCCTATGATT GATGACCAAT CAACCTGAAA GAAATCCCCA CATCTAATGT CGAATTTTC     1680
ATCATTTAAA AATATCTGTT TCTCTTTAAT TTTATCTAAA TAATTAGAGT TTATTTCAAT     1740
TCCAAAAATC TTTTTTGCTC TTGTAAACGA ATATGAAGCA GCCTCGATAA AATTTCCCAA     1800
GCCACAGGTT GGCTCAACTA TAATATCTGG ATTTACACCC AGTTGAACTA GCTTTTCGCA     1860
TACTTTTTCA GCTAATTCTA ACGGCGTTTG AAAATCTCCA TATTCTAATT TTGTTTTCTC     1920
AACATTATGA ATCATGGATT ATTTCTGTAA ACAGTAAGTA TGCCATCTTC TTGACCAGCA     1980
CGTTCTATTA CTCTTCCATA TTGAAGCCGC CACTGCAAAG CATTAGAAAT GGTCAAAAAT     2040
CCCTGCATAG GTGGATTTCT AAGTAATATC GCTGCGACGT TACCCGCCTC AATCTCATCG     2100
ACGGGTAAAT TACGATCGCT CATAAAGGCA ATTAAATCAT CTTTGTTACC TTCATTGGCC     2160
AAAATATTAC GGATTCCGCG AGTCATCTGG AAATCTGCTG TTCTTTCAGC ACTGACGTAA     2220
ATCGTATGCA AAATGTTTAG GGTTGCTGTG CGATTGGTAC TATTGTCTAT TTATCGTAG     2280
ACGAAAATCA GCAATGAATA CCCAAGCCCA AAAATCTTTT GCCGTGCAGA TTTGAACGGA     2340
CATGATGATT GTGGTTGTCT AATGCTTGTT ACCTTGACAT CTACTAGCAA CCCTGGAAAG     2400
TCAATACCGC TTGCAGAATT CCCCTGGACA AACTCATAGT GTTCTTTGAG ATAAAGTCTA     2460
AATTTTTGTT CTATGTATGT TCCGACTGCT TTCCCATCAG TAACACCGTA AAGCAATGGT     2520
TCTGGGTGTA TGGACTCGGC GGCTGAAAAT ATAGCTGCTT CTGTGCGAAG AGCTTCTATG     2580
GTCAAGATTG TCATGGGTAT AGCAAAAATT AGTGTAAAAA TTATAAATGC TATGTGCCTT     2640
GGAATTAACC ACTATAACTA TGAGACTTAG CATTTTGTA  GTGCGATCGC TAACCTGAGT     2700
CATTAGTGCG ATC                                                       2713
```

NSP7524V RESTRICTION-MODIFICATION GENES

This application is a continuation of now abandoned application, Ser. No. 08/014,468, filed Feb. 5, 1993, now abandoned.

Field of Industrial Application

This invention relates to a restriction enzyme and a modification enzyme which are useful as a reagent in the field of genetic engineering. More particularly, it relates to an Nsp7524V restriction-modification genes and a method for producing Nsp7524V restriction and/or modification enzymes.

PRIOR ART

Since Nsp7524V restriction-modification enzymes were isolated from Nostoc species PCC7524 in 1982, biochemical studies thereon have been conducted. The Nsp7524V restriction-modification enzymes consist of an Nsp7524V restriction enzyme having an activity of cleaving DNA and an Nsp7524V modification enzyme capable of protecting DNA from the cleavage by the Nsp7524V restriction enzyme. The Nsp7524V restriction enzyme is a typical type II restriction enzyme which recognizes a sequence consisting of six bases (5'-TTCGAA-3') in a symmetric structure in a DNA sequence and cleaves between T and C in the recognition sequence in such a manner as to give a fragment with a protruding 5' end.

On the other hand, the Nsp7524V modification enzyme is an enzyme which has an ability to protect DNA from the cleavage by the Nsp7524V restriction enzyme by methylating A in the above recognition sequence.

Examples of known processes for producing the Nsp7524V restriction enzyme include one reported by Reaston. He established a process for recovering the Nsp7524V restriction enzyme from the above Nostoc species PCC7524 (hereinafter referred to simply as the Nsp strain). This process is described in Gene, 20, 103–110 (1982). There has hitherto been reported no well-established, detailed process for producing the Nsp7524V modification enzyme.

However, only a small amount of the Nsp7524V restriction enzyme and the Nsp7524V modification enzyme was obtained from the Nsp strain and it was difficult to obtain a large amount of these enzymes. Further, since the Nsp strain produced other restriction enzymes and modification enzymes such as Nsp7524I, Nsp7524II, Nsp7524III, and Nsp7524IV simultaneously in addition to the Nsp7524V restriction enzyme and the Nsp7524V modification enzyme, a complicated procedure was to produce exclusively the Nsp7524V restriction enzyme and the Nsp7524V modification enzyme. Meanwhile, Nsp7524V restriction-modification genes have not been cloned so far.

Problems to be Solved by the Invention

It is an object of the present invention to provide Nsp7524V restriction-modification genes, to create a novel microorganism, in particular *Escherichia coli* which carries plasmids having, integrated thereinto, Nsp7524V restriction-modification genes and is suitable for the industrial production of the Nsp7524V restriction enzyme and the Nsp7524V modification enzyme, and to provide a process for producing the Nsp7524V restriction enzyme and the Nsp7524V modification enzyme by using this microorganism.

Means for Solving the Problems

To sum up, the present invention relates to Nsp7524V restriction-modification genes. The present invention also relates to a method for producing Nsp7524V restriction enzyme which comprises cultivating a microorganism carrying plasmids having, integrated thereinto, Nsp7524V restriction-modification genes, and recovering the Nsp7524V restriction enzyme thus produced from the culture.

The Nsp7524V restriction-modification genes involve a gene coding for the Nsp7524V restriction enzyme which has an activity of cleaving DNA and another gene coding for the Nsp7524V modification enzyme which has an ability to protect DNA from the cleavage by the Nsp7524V restriction enzyme.

The term "restriction-modification genes" as used herein means genes involving both of the restriction and modification enzyme genes as well as each of these genes. In other words, this term implies restriction and/or modification enzyme genes. Either one of these enzymes or a complex thereof may be used herein.

When plasmids having, integrated thereinto, both of the above genes are to be used, these genes may be integrated either into the same plasmid or separately into a number of plasmids.

The present inventors have succeeded in cloning DNA fragments containing Nsp7524V restriction-modification genes from the Nsp strain and, further, found out that, when a microorganism, in particular, *E. coli* carrying plasmids in which either the whole or part of these DNA fragments are integrated either into the same plasmid or separately into a number of plasmids is cultivated, a considerable amount of the Nsp7524V restriction enzyme and/or the Nsp7524V modification enzyme are accumulated in the cells and a large amount of the Nsp7524V restriction enzyme and/or the Nsp7524V modification enzyme can be isolated from the culture, thus completing the present invention.

Now, the present invention will be described in greater detail.

The novel microorganism according to the present invention, for example, *E. coli* may be obtained by the following steps which are given by way of example.

(1) Chromosomal DNA is extracted from the Nsp strain functioning as a DNA donor. Then a product of partial digestion of the chromosomal DNA with a restriction enzyme is ligated into a vector which has been previously cleaved with an appropriate restriction enzyme having the recognition sequence of the Nsp7524V restriction enzyme.

(2) An *E. coli* is transformed by the plasmid library prepared in the above step (1) and a plasmid library is obtained by the plasmid extraction method.

(3) The plasmid library prepared in the above step (2) is cleaved with the Nsp7524V restriction enzyme and uncleaved plasmids, namely, those in which the Nsp7524V modification enzyme is expressed are selected.

(4) The plasmid selected in the above step (3) is introduced into *E. coli* via transformation. The activity of the Nsp7524V restriction enzyme of the transformant is analyzed. As a result, the transformant has the activity and thus a novel microorganism capable of producing the restriction enzyme and the modification enzyme is obtained.

The chromosomal DNA of the Nsp strain is extracted from the cells recovered from the culture. The extraction, purification and cleavage with restriction enzymes of the chromosomal DNA of the Nsp strain can be done by any of well-known methods which are described in detail by Thomas et al., "*Procedures in Nucleic Acids Research*", page 535, published by Harper and Row (1966); and Sambrook et al., "*Molecular Cloning*", published by Cold Spring Harbor Laboratory (1989).

On the other hand, the plasmid vectors can be cleaved by similar methods. Usable plasmids involve well-known ones, for example, pACYC184. The plasmid pACYC184 contains the recognition sequence of the Nsp7524v restriction enzyme and the Nsp7524V modification enzyme gene can be easily screened by using it.

The chromosomal DNA is ligated into the vector by well-known methods.

A detailed description of the process for introducing plasmids into an *E. coli* host is reported by, for example, Hanahan in *Journal of Molecular Biology*, 166, 577 (1983).

Plasmids are prepared from an *E. coli* host by the alkali method. From among the plasmids thus prepared, those which code for the Nsp7524V modification enzyme gene and have been already expressed can be selected because they are protected from the cleavage by the Nsp7524V restriction enzyme. As a result, a plasmid containing a DNA fragment of approximately 2.7 kb originating in the Nsp strain is selected.

The selected plasmid containing the Nsp7524V modification enzyme gene is then introduced into *E. coli* via transformation to thereby create a novel microorganism, and analyzing the Nsp7524v restriction enzyme activity of the novel microorganism thus obtained.

The Nsp7524V restriction enzyme activity can be examined by the following in vitro method. A clone to be examined is cultivated and the cells are disrupted and ultracentrifuged. After removing the debris, the supernatant is subjected to a restriction enzyme reaction at 37° C. in a buffer solution [10 mM Tris-HCl (pH 8.0), 7 mM MgCl $_2$, 40 mM NaCl, 7 mM 2-mercaptoethanol, and 0.01% BSA] by using a λDNA as a substrate, followed by the analysis by agarose gel electrophoresis. When analyzed by this method, the above novel microorganism was found to exhibit an Nsp7524V restriction enzyme activity. Based on this fact, it is confirmed that the Nsp7524V restriction-modification genes have been successfully isolated.

A plasmid containing a DNA fragment coding for the Nsp7524V restriction-modification genes originating in the Nsp strain is named pNsp7524V. A novel microorganism obtained by integrating this plasmid into, for example, *E. coli* ED1648 strain by the transformation method is named *Escherichia coli* ED1648/pNsp7524V and deposited with Fermentation Research Institute of the Agency of Industrial Science and Technology under the accession number FERMB P-4638.

The DNA sequences of the DNA fragments inserted into pNsp7524V can be determined by, for example, preparing deletion mutants in accordance with the method of Yanisch-Perron and then effecting dideoxy method. The SEQ ID No. 1 in the sequence listing shows this DNA sequence.

In order to cultivate the novel microorganism thus obtained, ordinary conditions suitable for the growth of microorganisms belonging to the genus Escherichia can be employed.

In order to cultivate the above recombinant *Escherichia coli* ED1648/pNsp7524V and to recover the Nsp7524V restriction enzyme and Nsp7524V modification enzymes from the culture, the cells are collected from the culture and the enzymes are extracted by, for example, ultrasonication or ultracentrifugation and then purified by combining purification techniques such as nucleic acid removal, salting out, affinity chromatography, gel filtration and ion-exchange chromatography. Thus, a large amount of the Nsp7524V restriction enzyme and/or Nsp7524V modification enzyme can be obtained.

FIG. 1 shows the restriction map of a DNA fragment of about 2.7 kb containing the Nsp7524V restriction-modification genes.

EXAMPLES

In order to illustrate the present invention in greater detail, and not by way of limitation, the following Examples will be given.

Example 1

(1) Preparation of chromosomal DNA from Nsp strain

The Nsp strain was cultivated by the methods of Sutherland et al. [see *Journal of General Microbiology*, 155, 273–287 (1979)] and cells were collected by centrifugation. 2 g of the wet cells were suspended in 10 ml of a 25 mM Tris-HCl (pH 8.0)-50 mM glucose-10 mM EDTA solution. Lysozyme was dissolved in the same solution in such a manner as to give a concentration of 2 mg/ml and 1.0 ml of the resulting lysozyme solution was added to the above suspension. After stirring, the mixture was allowed to stand at 37° C. for 15 minutes. Next, 28 ml of a 100 mM NaCl-100 mM Tris-HCl (pH 8.0) solution was added thereto followed by stirring. Further, 4 ml of a 10% SDS solution was added and the mixture was stirred and allowed to stand at 37° C. for an hour. Then 1 ml of a 10% SDS-8% Sarcosyl solution was added thereto and the mixture was stirred and allowed to stand at 60° C. for 15 minutes. After allowing the solution to stand, the same volume of a mixture of phenol with chloroform (1:1) was added thereto. After slowly stirring for 10 minutes, the mixture was separated into an aqueous phase and a chloroform phase by centrifugation at 6,000×g for 10 minutes. Then the aqueous phase was taken up and the same amount of isopropyl alcohol was added thereto. After stirring, the mixture was allowed to stand at 0° C. for 10 minutes and then centrifuged at 13,500×g for 10 minutes. The precipitate thus formed was recovered, washed with 70% ethanol, dissolved in 10 ml of a TE solution [10 mM Tris-HCl (pH 8.0) and 1 mM EDTA] and stored at 4° C.

(2) Preparation of library

25 μg of the chromosomal DNA of the Nsp strain obtained in the above step (1) was reacted with 1 U of a restriction enzyme Sau3AI in a buffer solution [50 mM Tris-HCl (pH 7.5), 10 mM MgCl$_2$, and 1 mM dithiothreitol] at 37° C. for 1 to 10 minutes. Then the reaction mixture was electrophoresed on an agarose gel and fragments of 2 to 7 kb were recovered from the gel. These DNA fragments were ligated into pACYC184, which had been previously cleaved with BamHI, and then *E. coli* ED1684 was transformed by these plasmids. From the transformant thus obtained were prepared plasmids by the alkali method.

(3) Isolation of modification enzyme gene

When the plasmids obtained in the above step (2) were cleaved with the restriction enzyme Nsp7524V, those wherein the Nsp7524V modification enzyme had been expressed were not cleaved. Then *E. coli* ED1684 was transformed by the obtained mixture consisting of cleaved DNAs and uncleaved ones. Thus the uncleaved plasmids were exclusively introduced into the *E. coli*. Next, a transformant was selected by using a plate containing tetracycline and thus a transformant containing the Nsp7524v modification enzyme gene was obtained.

(4) Mesurement of the restriction activity

The plasmid selected in the above Example 1-(3) was reintroduced into *E. coli* ED1648 via transformation and Nsp7524V restriction activity was mesured in vitro. As a result, the activity was observed. Thus the *E. coli* strain carrying this plasmid was named *Escherichia coli* ED1648/pNsp7524V and deposited with Fermentation Research Institute of the Agency of Industrial Science and Technology under the accession number FERMB P-4638.

(5) Analysis of the structure of Nsp7524V restriction-modification genes

The DNA sequence of the DNA fragments inserted into pNsp7524V was determined by preparing deletion mutants with the use of Exonuclease III (Takara Shuzo) and Mung Bean Nuclease (Takara Shuzo) and then effecting the dideoxy method. The SEQ ID No. 1 in the sequence listing shows the DNA sequence.

Example 2

(1) Production of Nsp7524V restriction enzyme by the transformant

The *Escherichia coli* ED1648/pNsp7524V (FERM P-4638) obtained in the above Example 1-(6) was inoculated into 100 ml of an L medium containing 50 µg/ml of tetracycline and cultivated therein at 37° C. for ten hours. Then the cells were collected and suspended in 1.2 ml of a 20 mM potassium phosphate buffer solution (pH 7.5) containing 10 mM of 2-mercaptoethanol and 0.15% of Triton X-100. After disrupting of the cells by ultrasonication, the supernatant was recovered by ultracentrifugation at 10,000×g for 30 minutes. When the activities of the supernatant were measured, it was found out that 400,000 U of the Nsp7524V restriction enzyme and 8,000 U of the Nsp7524V modification enzyme were produced therein.

(2) Purification of Nsp7524V restriction enzyme *Escherichia coli* ED1648/pNsp7524V was inoculated into 500 ml of an L medium containing 50 µg/ml of tetracycline and cultivated therein at 37° C. for ten hours. After collecting, 10 g of the wet cells were suspended in 20 ml of a 20 mM potassium phosphate buffer solution (pH 7.5) containing 10 mM of 2-mercaptoethanol and 0.15% of Triton X-100. After disruption of the cells by ultrasonication, the supernatant was recovered by ultracentrifugation at 10,000×g for 30 minutes. Then the same amount of a buffer solution A [20 mM KPB (pH 7.5), 10 mM 2-mercaptoethanol, and 5% glycerol] was added thereto and the mixture was loaded on a phospho-cellulose column equilibrated with the same buffer solution. Then it was developed by linear gradient elution with 0 to 1 M potassium chloride and a fraction having an Nsp7524V restriction enzyme activity was recovered. Then, this fraction was dialyzed against a buffer solution B [10 mM KPB (pH 7.5), 10 mM 2-mercaptoethanol, and 5% glycerol] and loaded on an Affi-Gel Blue column (BIO-RAD) equilibrated with the same buffer solution. Then it was developed by linear gradient elution with 0 to 0.75M potassium chloride and approximately 5 ml of a fraction having an Nsp7524V restriction enzyme activity was recovered. This fraction was dialyzed against the buffer solution B again and loaded on a heparin-Sepharose column. Next, it was developed by linear gradient elution with 0 to 1M potassium chloride. The fraction having an Nsp7524V restriction enzyme activity thus recovered was loaded on a Sephadex G-100 column. The enzymatic activity of the active fraction thus obtained corresponded to approximately 1,000,000 U. This purified preparation was not contaminated with any other enzyme such as endonuclease, phosphatase or nonspecific DNase.

(3) Purification of Nsp7524V modification enzyme *Escherichia coli* ED1648/pNsp7524V was inoculated into 500 ml of an L medium containing 50 µg/ml of tetracycline and cultivated therein at 37° C. for ten hours. After collecting, 10 g of the wet cells were suspended in 30 ml of the buffer solution A. After disruption of the cells by ultrasonication, the supernatant was recovered by ultracentrifugation at 10,000×g for 30 minutes. Then a streptomycin sulfate solution was added to the supernatant in such a manner as to give a concentration of 2%. After stirring, the supernatant was recovered by centrifugation. Next, an ammonium sulfate powder was added thereto in such a manner as to achieve 65%-saturation and then recovered by ultracentrifugation at 13,500×g for 30 minutes. The precipitate thus recovered was suspended in the buffer solution B [10 mM KPB (pH 7.5), 10 mM 2-mercaptoethanol, and 5% glycerol] and dialyzed against the buffer solution B. Then it was loaded on a heparin-Sepharose column equilibrated with the buffer solution B and developed by linear gradient elution with 0.05 to 0.80M sodium chloride. A fraction having an Nsp7524V modification enzyme activity was recovered and dialyzed against the buffer solution B. Then it was loaded on a DEAE-Sephadex (A-50) column equilibrated with the buffer solution B and developed by linear gradient elution with 0.05 to 0.60M sodium chloride. Then a fraction having an Nsp7524V modification enzyme activity was recovered and dialyzed against the buffer solution B. Then it was loaded on a phospho-cellulose column which had been previously equilibrated with the buffer solution B and developed by linear gradient elution with 0.05 to 1.0M sodium chloride. The enzymatic activity of the active fraction thus obtained corresponded to approximately 30,000 U. This purified preparation was not contaminated with any other enzyme such as endonuclease, phosphatase or nonspecific DNase.

Effect of the Invention

As has been described above in detail, Nsp7524V restriction-modification genes are isolated according to the present invention. The use of an *E. coli* strain transformed with a plasmid containing these genes makes it possible to produce the Nsp7524V restriction enzyme and/or Nsp7524V modification enzyme, which are useful in the field of genetic engineering, at a high efficiency.

What is claimed is:

1. Isolated DNA coding for the Nsp7524V restriction enzyme, wherein the isolated DNA is obtainable from the vector pNsp7524V.

2. A recombinant DNA vector comprising a vector into which a DNA segment coding for the Nsp7524V restriction enzyme produced by Nostoc species PCC7524 has been inserted.

3. Isolated DNA coding for the Nsp7524V modification enzyme, wherein the isolated DNA is obtainable from the vector pNsp7524V.

4. A cloning vector which comprises the isolated DNA of claim 1.

5. A cloning vector which comprises the isolated DNA of claim 3.

6. A cloning vector of claim 4, wherein the cloning vector comprises pNsp7524V.

7. A host cell transformed by the vector of claim 4, 5, or 6.

8. A method of producing Nsp7524V restriction enzyme comprising culturing a host cell transformed with the vector of claim 4, 5, or 6 under conditions suitable for the expression of said enzyme.

* * * * *